United States Patent [19]

Aslam et al.

[11] Patent Number: 4,933,495

[45] Date of Patent: Jun. 12, 1990

[54] PROCESS FOR THE PRODUCTION OF 3-MONO OR 3,5 DIHALOGENATED 4-ACETOXYSTYRENE, ITS POLYMERIZATION, AND HYDROLYSIS

[75] Inventors: Mohammad Aslam, Corpus Christi, Tex.; Richard Vicari, Chatham Township, Morris County, N.J.; Ralph Dammel, Mainz-Bretzenheim, Fed. Rep. of Germany; Juergen Lingnau, Mainz-Laubenheim, Fed. Rep. of Germany; Karl-Friedrich Doessel, Wiesbaden, Fed. Rep. of Germany

[73] Assignee: Hoechst Celanese Corporation, Somerville, N.J.

[21] Appl. No.: 384,181

[22] Filed: Jul. 24, 1989

Related U.S. Application Data

[62] Division of Ser. No. 312,170, Feb. 21, 1989, Pat. No. 4,868,257.

[51] Int. Cl.$^5$ .................. C07C 49/115; C07C 39/24
[52] U.S. Cl. ........................ 568/309; 568/774
[58] Field of Search .............. 568/309, 774; 526/75; 525/328.6, 328.7

[56] References Cited

PUBLICATIONS

Hewgill & Smith "An Alternative Route to Stable Aryloxy Polyradicals", Journal of Polymer Science vol. 14, 1976, pp. 463–465.

Isaks et al., "Photohydration via Intramolecular Proton Transfer to Carbon in Electonically Excited Sates", J. Chm. Society, 1984, vol. 106, pp. 2728–2730.

*Primary Examiner*—Joseph L. Schofer
*Assistant Examiner*—Jeffrey T. Smith
*Attorney, Agent, or Firm*—D. R. Cassady; R. S. Roberts; R. Plottel

[57] ABSTRACT

The present invention relates to a process for the production of 3-mono or 3,5-disubstituted-4-acetoxystyrene wherein the 3- or 3,5-substitution is independently $C_1$ to $C_{10}$ alkyl, chlorine, bromine, iodine, —$NO_2$, —$NH_2$, or —$SO_3H$, a process for its polymerization, hydrolysis, and use in a variety of compositions.

7 Claims, No Drawings

PROCESS FOR THE PRODUCTION OF 3-MONO OR 3,5 DIHALOGENATED 4-ACETOXYSTYRENE, ITS POLYMERIZATION, AND HYDROLYSIS

This is a division of copending application Ser. No. 07/312,170, filed on 2/21/89, now U.S. Pat. No. 4,868,257.

BACKGROUND OF THE INVENTION

The present invention relates to a process for the production of 3-mono or 3,5-disubstituted-4-acetoxystyrene wherein the 3- or 3,5-substitution is independently $C_1$ to $C_{10}$ alkyl, chlorine, bromine, iodine, $-NO_2$, $-NH_2$, or $-SO_3H$; a process for its polymerization, and hydrolysis. In its most preferred form, the invention relates to 3-mono- and 3,5-dihalogenated 4-acetoxystyrenes which contain chlorine or bromine as the halogen, and a method of preparation thereof. 3,5-dibromo-4-hydroxystyrene compounds have been known for a long time and were initially prepared from 4-hydroxycinnamic acid by (a) bromination of positions 3 and 5 on the ring as well as addition of bromine to the double bond,
(b) dehydrobromination with concurrent decarboxylation, leading to reconstitution of the vinylic double bond,
(c) then, addition of hydrogen bromide to said double bond to form a saturated vicinal dibromide,
(d) finally, by debromination for reconstitution of the vinylic double bond (see Liebigs Annalen der Chemie, 322, 235 (1902)) as shown in the following scheme:

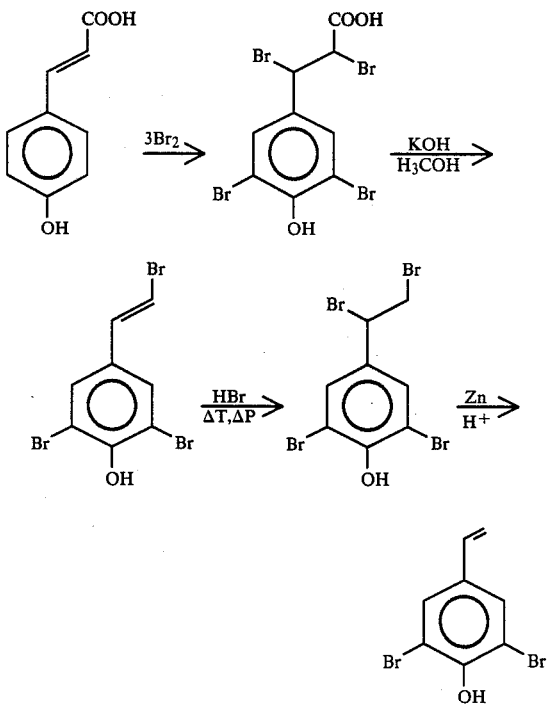

The existing process, based on cinammic acid derivatives, does however have considerable disadvantages in terms of the preparation method. In particular, the decarboxylation necessary in this method proves to be disadvantageous. Moreover, out of 7 bromine atoms required in the course of this synthesis, only 2 remain in the final product. It was therefore desirable to develop a synthesis making more economical use of bromine.

It is known in the art to produce monomers, homopolymers and copolymers of unsubstituted 4-acetoxystyrene and to hydrolyze the same to produce 4-hydroxystyrene derivatives or polyvinyl phenols. Such find use in the production of photoresists, adhesives, coating compositions and the like. In particular, polymers or copolymers prepared from non-halogenated monomers are used for preparing coating compositions and as binders for photoresists. In this connection, reference is made to post-brominated poly(4-hydroxy)styrenes which are used in accordance with German patent application P No. 37 30 784.3 as radiation-sensitive compounds in corresponding photoresists. The monomeric acetoxystyrene of this invention finds use as an intermediate in the production of such polymers as poly(3-mono or 3,5 dimethyl-4-acetoxystyrene) and poly(3-mono or 3,5-dimethyl-4-hydroxystyrene). These later compounds are useful as improved binder resins for photoresists which have a more advantageous dissolution rate in commercially accepted photoresist developers, and are more fully described in U.S. patent application Ser. No. 097,815 filed on Sept. 16, 1987 and which is incorporated herein by reference.

Alpha acetoxystyrene and beta acetoxystyrenes are described in U.S. Pat. No. 4,144,063 and acetoxymethylstyrene is taught in U.S. Pat. No. 3,963,495. U.S. Pat. No. 4,075,237 describes 1,4-dimethyl-2-hydroxystyrene, while U.S. Pat. No. 4,565,846 teaches the use of poly(3,5-dimethyl-4-hydroxystyrene). Japanese patent No. 84023747 describes anti-static compounds employing poly-acetoxymethylstyrene and U.S. Pat. No. 4,221,700 describes a stabilized synthetic polymer composition using poly(alkylated alkenylphenol) including 2-methyl paravinyl phenol. U.S. Pat. Nos. 4,600,683 and 4,543,397 describe poly (alphamethyl vinylphenol). U.S. Pat. Nos. 4,517,028; 4,460,770 and 4,539,051 describe dimethyl vinyl phenol. One preferred product of this invention is 3,5-dibromo-4-hydroxystyrene which is particularly useful as a binding resin for o-quinone diazides in the production of x-ray sensitive photoresists.

SUMMARY OF THE INVENTION

The invention provides a process for the production of 3-mono or 3,5-disubstituted-acetoxystyrene which comprises:

(a) acylating phenol to produce 4-hydroxyacetophenone; and
(b) reacting the 4-hydroxyacetophenone with a reagent under conditions to form 3-mono or 3,5-disubstituted-4-hydroxyacetophenone; and
(c) esterifying the 3-mono or 3,5-disubstituted-4-hydroxyacetophenone, preferably with acetic anhydride, to form 3-mono or 3,5-disubstituted-4-acetoxyacetophenone; and
(d) reducing the 3-mono or 3,5-disubstituted-4-acetoxyacetophenone with a sufficient amount of a reducing agent to produce 1-(3'-mono or 3',5'-disubstituted-4,-acetoxyphenyl)ethanol; and
(e) dehydrating the 1-(3'-mono or 3',5'-disubstituted-4'-acetoxyphenyl)ethanol to produce 3-mono or 3,5-disubstituted-acetoxystyrene; wherein said substitutions are selected from the group consisting of Cl, Br, I, $NO_2$, $NH_2$, $SO_3H$, or $C_1$-$C_{10}$ alkyl. The invention also provides a process for the production of poly(3-mono or 3,5-disubstituted-4-acetoxystyrene) which comprises:

(a) acylating phenol, preferably with acetic anhydride and using HF as a catalyst to produce 4-hydroxyacetophenone; and (b) reacting the 4-hydroxyacetophenone with a reagent under conditions to form 3-mono or 3,5-disubstituted-4-hydroxyacetophenone; and (c) esterifying the 3-mono or 3,5-disubstituted-4-hydroxyacetophenone, preferably with acetic anhydride to form 3-mono or 3,5- disubstituted-4-acetoxyacetophenone; and (d) reducing the 3-mono or 3,5-disubstituted-4'-acetoxyacetophenone with a sufficient amount of a reducing agent to produce 1-(3,-mono or 3',5'-disubstituted-4'-acetoxyphenyl)ethanol; and (e) dehydrating the 1-(3,-mono or 3',5'-disubstituted-4'-acetoxyphenyl)ethanol to produce 3-mono or 3,5-disubstituted-acetoxystyrene; and (f) free radical polymerization of the 3-mono or 3,5-disubstituted-4-acetoxystyrene to form poly(3-mono or 3,5-disubstituted-4-acetoxystyrene) having a molecular weight in the range of from about 1,000 to about 800,000, preferably about 5,000 to about 500,000;

wherein said substitutions are selected from the group consisting of Cl, Br, I, $NO_2$, $NH_2$, $SO_3H$, or $C_1$–$C_{10}$ alkyl. The invention still further provides a process for the production of poly(3-mono or 3,5-disubstituted-4-hydroxystyrene) which comprises:

(a) acylating phenol, preferably with acetic anhydride to produce 4-hydroxyacetophenone; and (b) reacting the 4-hydroxyacetophenone with a reagent under conditions to form 3-mono or 3,5-disubstituted-4-hydroxyacetophenone; and (c) esterifying the 3-mono or 3,5-disubstituted-4-hydroxyacetophenone, preferably with acetic anhydride to form 3-mono or 3,5-disubstituted-4-acetoxyacetophenone; and (d) reducing the 3-mono or 3,5-disubstituted-4-acetoxyacetophenone with a sufficient amount of a reducing agent to produce 1-(3'-mono or 3',5'-disubstituted-4'-acetoxyphenyl)ethanol; and (e) dehydrating the 1-(3'-mono or 3',5'-disubstituted-4'acetoxyphenyl)ethanol to produce 3-mono or 3,5-disubstituted-4-acetoxystyrene; and (f) free radical polymerization of the 3-mono or 3,5-disubstituted-4-acetoxystyrene to form poly(3-mono or 3,5-disubstituted-4-acetoxystyrene) having a molecular weight in the range of from about 1,000 to about 800,000, preferably about 5,000 to about 500,000; and (g) hydrolyzing the poly(3-mono or 3,5-disubstituted-4-acetoxystyrene) to form poly(3-mono or 3,5-disubstituted-4-hydroxystyrene) having a molecular weight in the range of from about 1,000 to about 500,000, preferably about 5,000 to about 500,000;

wherein said substitutions are selected from the group consisting of Cl, Br, I, $NO_2$, $NH_2$, $SO_3H$, or $C_1$–$C_{10}$ alkyl.

In one more preferred form of the invention there is provided a method for preparing 3-mono- and 3,5-dihalogenated 4-hydroxy- and 4-acetoxystyrenes, which comprises:

(a) halogenation of a 4-hydroxyacetophenone with general formula

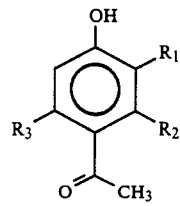

wherein $R_1$ is hydrogen or alkyl, in particular $C_1$–$C_{10}$ alkyl, and $R_2$ and $R_3$ are independently hydrogen, alkyl, alkoxy, or halogen, wherein $R_1$ and $R_2$ may also be combined to form a cycloaliphatic ring, consisting in particular of 6 to 12 members; and (b) esterification (protection) of the hydroxyl function to form a halogenated 4-acetoxyacetophenone derivative; and (c) reduction of the ketone function to a hydroxyl function, (d) dehydration to form 3-mono or 3,5-dihalogenated 4-acetoxystyrene, and where appropriate (e) hydrolysis of the protective group to form the 3-mono or 3,5-dihalogenated 4-hydroxystyrene.

Halogenation is preferable chlorination or bromination, but most preferably bromination.

In the preferred embodiment, the compounds with general formula I, have the following substituents:

$R_1$ is hydrogen or ($C_1$–$C_3$) alkyl, especially methyl; and $R_2$ and $R_3$ are preferably the same and are hydrogen, ($C_1$–$C_3$) alkyl, ($C_1$–$C_3$) alkoxy, or bromine.

Compounds with general formula I which contain hydrogen for $R_2$ and $R_3$ are particularly preferred. When $R_1$ is hydrogen, the extent of halogenation (i.e. whether a 3-monohalo product or a 3,5-dihalo product is formed) depends on the molar ratio of halogen to the compound with general formula I that is used.

DETAILED DESCRIPTION OF THE PREFERRED EMBODIMENT

In the preferred embodiment, the monomers are 3,5-disubstituted and the preferred substitution is dibromo. The preferred embodiment will now be described in detail. The other substitutions are obtained analogously.

In the process for the production of 3,5-dibromo-4-acetoxystyrene, one begins with phenol and acylates it, preferably with acetic anhydride via a Friedel-Crafts catalysis or Fries rearrangement to produce 4-hydroxyacetophenone. This is then reacted with a sufficient amount of bromine to produce the desired 3- or 3,5-substitution. In the preferred embodiment, the substitution is 3,5-dibromo, therefore the 4-hydroxyacetophenone is reacted with two molar equivalents of bromine. This 3,5-dibromo-4-hydroxyacetophenone is then esterified with acetic anhydride to form 3,5-dibromo-4-acetoxyacetophenone. The latter is then reduced to form 1-(3',5'-dibromo-4'-acetoxyphenyl)ethanol. This is then dehydrated with an acid or base to form 3,5-dibromo-4-acetoxystyrene monomer. A typical reaction sequence may be described schematically as follows:

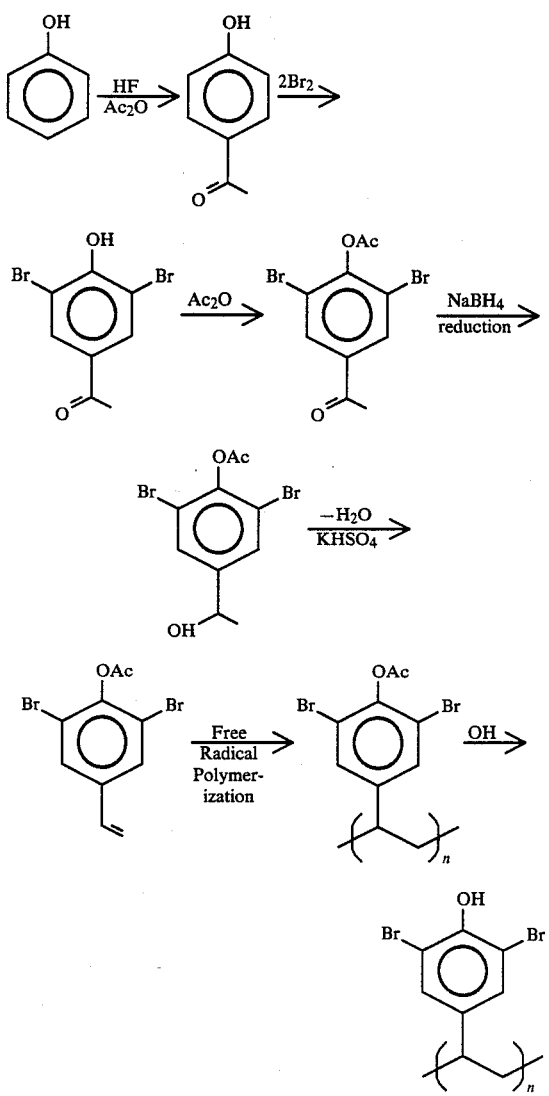

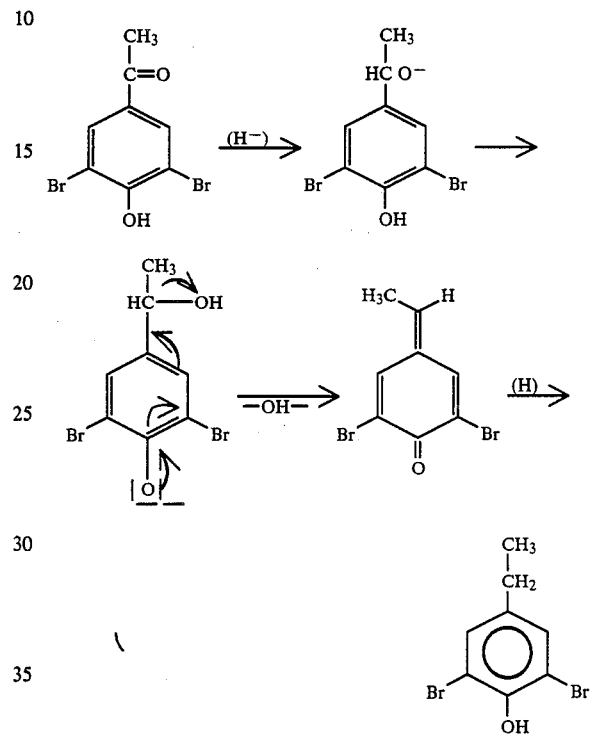

In the preferred embodiment the first reaction steps proceed as follows. That is, one charges the reaction vessel with, a slight excess of acetic anhydride and a Friedel-Crafts catalyst such as hydrogen fluoride. The acylation is conducted at a temperature of from about 5° C. to about 100° C., or more preferably from about 20° C. to about 80° C. A most preferred temperature is about 50° C. The reaction proceeds at a preferred pressure of from about 700 mm Hg to about 780 mm Hg for from about 1 to about 5 hours. Although hydrogen fluoride is the preferred catalyst, other Lewis acids may be also used such as $AlCl_3$, $BF_3$, $HClO_4$, $FeCl_3$ and $SnCl_4$. In the alternative, the acylation may be conducted by a Fries rearrangement, in a manner well known to the skilled artisan. The reaction product 4-hydroxyacetophenone is then reacted with a sufficient amount of a reagent to produce the desired 3- or 3,5-substitution. Although bromine is used in the preferred embodiment, in order to obtain the other substituents of this invention, the other preferred reactants non-exclusively include chlorine, iodine, nitric acid, sulfuric acid and $C_1$ to $C_{10}$ alkyl halides.

Attempts to directly reduce the keto functionality in 3,5-dibrominated 4-hydroxyacetophenone by means of e.g. catalytic the hydrogenation or complex hydrides, as known to the skilled artisan, invariably lead to overreduction with exclusive formation of 3,5-dibromo-4-ethylphenol.

While not wishing to be bound by theory it is believed that this behavior is caused by formation of quinonemethide intermediates which are then preferentially reduced at the methide carbon as shown in the following scheme:

This undesirable behavior can be pre-empted by obviating phenolate ion formation, which is essential to the above mechanism. This is most easily prevented by protecting the phenolic functionality, e.g. by esterification.

Esterification of the hydroxyl group for its protection is preferably accomplished with acetyl chloride or with acetic anhydride. However, any reagents known to protect hydroxyl functions can be used. These include in particular the formation of ethers, such as methyl, methoxymethyl, 2-methoxyethoxymethyl, methylchiomethyl, tetra-hydropyranyl, cyclopropylmethyl, allyl, isopropyl, cyclohexyl, t-butyl, benzyl, o-nitrobenzyl, 9-anthrylmethyl, and 4-picolyl ethers, but also silyl ethers, such as trimethylsilyl and t-butyldimethylsilyl ethers, esters such as acetates, pivaloates, benzoates, and 9-fluorene-carboxylates, carbonates such as methyl, 2,2,2-trichloroethyl, vinyl, and benzyl carbonates, arylcarbamates, and sulfonates such as methanesulfonates and toluenesulfonates. Protective groups of this type are described by Theodora W. Green, Protective Groups in Organic Synthesis, John Wiley & Sons, 1981. However, the acetoxy group is particularly preferred.

This mono- or disubstituted hydroxyacetophenone is then esterified under conditions as stated before. The most preferred reagent is acetic anhydride. In this process, the 3,5-dibromo-4-hydroxyacetophenone is refluxed with an excess of acetic anhydride for from about 15 to about 20 hours. Excess acetic anhydride as well as generated acetic acid are removed by distillation in vacuo. This is conducted, for example at a pressure of from about 0.1 to about 760 mm Hg and at a temperature of from about 15° C. to about 40° C., preferably from about 30° C. to about 35° C.

The resultant 3,5-dibromo-4-acetoxyacetophenone is then preferably recrystallized from an appropriate recrystallization solvent, preferably an alcohol, and most preferably isopropanol. The 3,5-dibromo-4-acetoxyacetophenone is then reduced with a suitable reducing agent to form 1-(3',5'-dibromo- 4'-acetoxyphenyl)ethanol. One preferred reducing agent is NaBH$_4$. Other reducing agents non-exclusively include lithium aluminum hydride, hydrogen, and diisobutyl aluminum hydride. The subsequent reduction of the ketone function can also be done with other complex hydrides and by catalytic reduction with hydrogen. Lithium borohydride is also possible as well as reaction products that arise for example upon dissolution of sodium borohydride or lithium borohydride in alcohols. The preferred reaction medium in reduction with complex hydrides is ethanol or mixtures of organic solvents miscible with water, such as THF/water mixtures. The most preferred solvent is ethanol. This product is then dehydrated. Dehydration is preferably conducted by vacuum heating in the presence of a polymerization inhibitor and a dehydrating agent. In one preferred embodiment, the 1-(3',5'-dibromo-4'-acetoxyphenyl)ethanol is mixed with a KHSO$_4$ dehydrating agent and t-butyl catechol as a polymerization inhibitor. Other useful dehydrating agents non-exclusively include bases, CuSO$_4$, CuCl$_2$ and Al$_2$O$_3$. Other polymerization inhibitors non-exclusively include hydroquinone, tetrachloroquinone and di-t-butyl-p-cresol. The dehydrating agent is present in an amount of from about 0.25 to about 5.0 percent weight of the ethanol. The polymerization inhibitor is preferably present in an amount of from about 0.01% to about 5% based on the weight of the ethanol. The reaction vessel is heated to from about 160° C. to about 210° C., preferably 168° C. to about 190° C. at a pressure of from about 0.01 to about 0.1 mm Hg. The resultant product is 3,5-dibromo-4-acetoxystyrene. The 3,5-dibromo-4-acetoxystyrene monomer is then polymerized by a free radical initiation process to produce poly(3,5 dibromo-4-acetoxystyrene) such that it has a molecular weight in the range of from about 1,000 to about 800,000, preferably 5,000 to 500,000 or more, preferably about 5,000 to about 300,000. This intermediate is then hydrolyzed with a base or acid to form poly(3,5-dibromo-4-hydroxystyrene) such that it also has the molecular weight range of from about 1,000 to about 500,000, preferably about 5,000 to about 500,000.

One preferred free radical initiator is azoisobutyronitrile. Other azo type initiators are also suitable. Still others non-exclusively include peroxides such as benzoyl peroxide, and di-t-butyl peroxide. It is predicted that essentially any free radical initiation system will serve in the same fashion. One preferred hydrolyzing agent is tetramethyl ammonium hydroxide. Other hydrolyzing agents non-exclusively include aqueous NH$_3$, NaOH, KOH, HCl, and H$_2$SO$_4$.

The following non-limiting examples serve to illustrate the invention.

EXAMPLE 1

3,5-Dibromo-4-hydroxyacetophenone

4-Hydroxyacetophenone (110.8 g, 0.81 mol) is dissolved in 50% acetic acid (1200 ml) and cooled in an ice bath. A solution of bromine (281.6 g, 1.76 mol) in 80% acetic acid is added dropwise to the 4-hydroxyacetophenone solution over a period of four hours. The reaction temperature is maintained below 25° C. After the bromine addition is complete, a white solid precipitates. The solid is collected via filtration and washed with water. Recrystallization with isopropyl alcohol affords a white to light pink crystalline solid. The crystals are dried in a vacuum oven at room temperature to afford 178.5 g of 3,5-dibromo-4-hydroxyacetophenone.

3,5-Dibromo-4-acetoxyacetophenone 3,5-Dibromo-4-hydroxyacetophenone (154.0 g, 0.523 mol), acetic anhydride (100.0 ml) and sodium acetate (1.0 g) are placed in a one liter flask and heated to reflux overnight. Unreacted acetic anhydride and acetic acid are removed via distillation at 0.1–0.25 mm Hg. A solid material is left in the flask.

Recrystallization with isopropyl alcohol (110 ml) affords a light yellow crystalline solid. The crystals are dried in a vacuum oven to yield 161.8 g of 3,5-dibromo-4-acetoxyacetophenone.

1-(3',5'-Dibromo-4'-acetoxyphenyl)ethanol 3,5-Dibromo-4-acetoxyacetophenone (35.2 g, 0.1 mol) is suspended in absolute alcohol (100 ml). The flask is cooled in ice and sodium borohydride (1.9 g, 0.05 mol) is added slowly to the cooled reaction mixture. The reaction mixture is stirred at 0° C. for two hours. Water (300 ml) is added and the product is extracted with ethyl acetate (300 ml). The organic layer is separated, dried over magnesium sulfate and concentrated on the rotary evaporator to yield 30.7 g of 1-(3',5'-dibromo-4'-acetoxyphenyl)ethanol.

3,5-Dibromo-4-acetoxystyrene 1-(3',5'-Dibromo-4'-acetoxyphenyl)ethanol (104.86 g, 0.296 mol) KHSO$_4$ (1.0 g) and t-butyl catechol (3.34 g) are mixed in a flask. The flask is equipped with a fractional distillation apparatus and attached to a vacuum pump. Dehydration is conducted at 168°–187° C. under vacuum (0.05–0.10 mm Hg). The product is distilled at 116°–134° C. to yield an oily solid (61.82 g). Recrystallization from hexane gives white crystals, m.p. 76° C.

EXAMPLE 2

Polymerization 5 g of 3,5-dibromo-4-acetoxystyrene is combined with 25 ml of degassed tetrahydrofuran and 0.2g of azoisobutyronitrile as the free radical initiator. The reaction is conducted for 15 hours at 70° C. under nitrogen. The polymer is isolated by precipitation into water and filtering to yield a poly(3,5-dibromo- 4-acetoxystyrene) having an average molecular weight of 3,700.

EXAMPLE 3

Hydrolysis

The reaction product of example 2 is hydrolyzed by mixing with 1 ml tetramethyl ammonium hydroxide, and 10 ml methanol. The mixture is heated to 70° C. for 15 hours under nitrogen. The polymer is isolated by precipitating into water and filtering to yield poly(3,5-dibromo-4-hydroxystyrene).

EXAMPLE 4

3,5-Dibromo-4-hydroxyacetophenone

A solution of 320 g or 103 ml (2 moles) bromine in 50 ml acetic acid is added dropwise to a suspension of 136 g (1 mole) 4-hydroxyacetophenone and 164 g (2 moles) sodium acetate in such a way that the temperature does not rise above 30° C. After the bromine solution has been completely added, the reaction mixture is stirred for a further 20 minutes following which it is poured into 2 liters of ice water and finally the solid product is removed by filtration. The product is rinsed with water and recrystallized after drying from toluene or ethyl acetate. A yield of 91% may be achieved. The vacuum-dried crystals have a melting point of 180°–184° C.

EXAMPLE 5

3,5-Dibromo-4-acetoxyacetophenone 15.7 g (0.2 mole) acetylchloride is added dropwise to a stirred mixture of 57.1 g (0.194 mole) 3,5-dibromo-4-hydroxyacetophenone, 1.67 g 4-dimethylaminopyridine, and 19.6 g triethylamine in toluene at 60½° C. After four hours of further reaction under the given conditions, the hydrochloride precipitated from the solution is filtered off and the toluene solvent is distilled from the remaining solution under vacuum and the remaining product is recrystallized from a mixture of diisopropyl ether and activated charcoal. A yield of 93% may be achieved. The white, isolated crystals have a melting point of 114° C.

EXAMPLE 6

1-(3',5'-Dibromo-4'-acetoxyphenyl)ethanol 5 g of sodium borohydride is added in small portions to an ice-cooled solution of 84 g (0.25 mole) 3,5-dibromo-4-acetoxyacetophenone in tetrahydrofuran and water. The reaction is exothermic. When all the sodium borohydride has been added and after a further 30 minutes of stirring, the reaction mixture is nearly clear. The solution is brought to a pH of 2 with 2 g hydrochloric acid, the solution is extracted twice with ether, and the combined organic phases are rinsed twice with water. After drying the ether solution, the solution is concentrated under vacuum. A yellow oil is produced, which in a high vacuum has a boiling point of 132°–139° C. at 0.002 Torr (mbar). The yield of this reaction stage after distillation is 80 g of a colorless oil.

EXAMPLE 7

3,5-Dibromo-4-acetoxystyrene

A mixture of 67.6 g (0.02 mole) 1-(3',5'-dibromo-4'-acetoxyphenyl)ethanol, 0.35 g freshly melted and then finely pulverized potassium hydrogen sulfate, and 0.5 g t-butylhydroquinone are heated at 20 Torr to 170°–190° C. The resulting product is distilled off (under vacuum) at a temperature of 140° to 160° C. It is taken up in ether, the ether solution is washed with $Na_2CO_3$, dried, and concentrated under vacuum. The remaining product is distilled at 0.02 mbar; the boiling point is 116° C. The isolated product, which is a highly viscous oil or a white, waxy solid, has a melting point of approximately 75° C. The reaction yield is 27 g.

EXAMPLE 8

Preparation of 3,5-Dibromo-4-hydroxystyrene 10 g of 4-acetoxy-3,5-dibromostyrene are dissolved in 50 ml THF and 25 ml methanol, 12 g hydrazine hydrate (80% aqueous solution) is added, and the cloudy mixture is then converted into a clear solution by adding 3 ml of water. After 40 minutes it is acidified with a semi-concentrated HCl to pH 2 and extracted twice with ether, the ether phase is washed twice with water and dried over sodium sulfate, and the ether is removed with a rotary evaporator at room temperature under aspirator vacuum. 8.5 g of crude product remain, from which 6.45 g of white crystals (mp 74° C.) are obtained by recrystallization from petroleum ether.

EXAMPLE 9 o-Cresyl Acetate

First 235.5 g (3.3 moles) acetyl chloride then 282.8 g (2.8 moles) triethylamine are added dropwise to a mixture of 324 g (3 moles) o-cresol and 36.6 g (0.3 mole) 4-dimethylaminopyridine in 1 liter of toluene. The mixture is then heated for 3 h at 65° C. The resulting solid hydrochloride is separated by filtration and the organic phase is washed twice with 1 N hydrochloric acid then with water. The solution is dried and then the solvent is recovered under vacuum. The remaining oil is distilled under vacuum. It has a boiling point of 87° C. at 12 Torr. The yield is 428.8 g.

EXAMPLE 10

4-Hydroxy-5-methylacetophenone

A total of 360 g dry AlCl3 is added to a mixture of 300 g (2 moles) o-cresyl acetate and 1.2 liters nitrobenzene in small portions. The reddish mixture is kept at room temperature with moisture excluded for 12 h, and the mixture increasingly takes on a dark-green color. When the reaction mixture is poured into ice water, a light yellow emulsion is obtained, to which the quantity of a 10% hydrochloric acid needed to make it clear is added. After 1 liter of ether has been added, two phases form, from which the ether phase is separated and washed with a 7.5% potassium hydroxide solution. The aqueous phase is combined with the potassium hydroxide solution, acidified, and the resulting product, after extraction with ether, drying, and recrystallization from diisopropyl ether, is isolated. The light-brown product has a melting point of 108° to 109° C. The reaction yield is 122.8 g.

EXAMPLE 11

3-Bromo-4-hydroxy-5-methylacetophenone 110 g (0.73 mole) 4-hydroxy-5-methylacetophenone is suspended in a mixture of 370 ml acetic acid (glacial) and 370 ml $H_2O$, the mixture is cooled to 5° C., and a solution of 116.8 g or 38 ml (0.73 mole) bromine in 100 ml acetic acid is added dropwise while cooling such that the temperature does not rise above 10° C. Addition of bromine takes about 1 h. After cooling for a further 2 h at room temperature, the product is filtered off, dried, and recrystallized from acetonitrile. 150 g of product with a melting point of 145°–146° C. can be isolated.

EXAMPLE 12

3-Bromo-4-acetoxy-5-methylacetophenone 52 g or 47 ml (0.66 mole) acetyl chloride are added dropwise to a solution of 140 g (0.6 mole) 3-bromo-4-hydroxy-5-methylacetophenone, 7.4 g 4-dimethylaminopyridine and 60.6 g (0.6 mole) triethylamine in 500 ml toluene. The resulting reaction mixture is stirred for another 3 h at 65° C. The hydrochloride formed is filtered off and the toluene phase is washed twice with 2 N hydrochloric acid then twice with water. After drying and distillation of the solvent under vacuum, 99 g of pure product is isolated. The white crystals have a melting point of 78°–80° C.

EXAMPLE 13

1-(3'-Bromo-4'-acetoxy-5'-methylphenyl)ethanol 99 g (0.37 mole) of 3-bromo-4-acetoxy-5-methylacetophenone is added to 250 ml of tetrahydrofuran and cooled to 0° C. 20 ml water is added and then 7 g (0.185 mole) sodium borohydride is added while cooling in portions such that the temperature does not exceed 20° C. After two hours stirring at room temperature, the reaction mixture is added to a mixture consisting of 100 ml concentrated hydrochloric acid, 200 ml water, and 250 g ice, the mixture is thoroughly stirred, and then extracted with ether. The ether phase is washed first with a 5% sodium carbonate solution then with water. After distilling the solvent, 96.3 g of a viscous oil is obtained as the crude product, and this is then distilled under vacuum according to H3 and yields 86.8 g of product.

EXAMPLE 14

3-Bromo-4-acetoxy-5-methylstyrene

A mixture of 28 g 1-(3'-bromo-4'-acetoxy-5'-methylphenyl)ethanol and 0.5 g freshly prepared potassium hydrogen sulfate is heated under a 20 Torr vacuum to 190°–200° C. The distillate is transferred to an ice-filled reaction vessel which contains 2 g t-butylhydroquinone. After 2 h, the distillate is taken up in ether, the ether phases are treated with a 5% sodium carbonate solution and dried, then the solvent is distilled off under vacuum. At 0.05 Torr, 6.8 g of an impure product is obtained at a temperature of 86 to 89° C., from which 18 g of pure monomer can be obtained.

EXAMPLE 15

Attempted direct reduction of 3,5-dibromo-4-hydroxyacetophenone 10 g of 3,5-dibromo-4-hydroxyacetophenone are dissolved in methanol, cooled to 0° C., at which point the calculated amount of sodium boron hydride is slowly added with stirring. After one minute, thin layer chromatography shows the presence of 4-ethylphenol, but not of 1-(3',5'-dibromo-4,-hydroxyphenyl)ethanol (by comparison with authentic samples). After one hour, the mixture is worked up by pouring into water, extracting the ether, and drying on a rotary evaporator. Analysis of the products by NMR spectroscopy shows the material to be a mixture of starting material and 4-ethylphenol, with no alcohol reduction product present.

Similar results are obtained with other solvents and complex hydrides as well as with attempted catalytic hydrogenations.

EXAMPLE 16

Dehydration of 1-(3',5'-dibromo-4'-acetoxyphenyl)ethanol with copper (II) sulfate 5 g 1-(3',5'-dibromo-4-acetoxyphenyl)ethanol are dissolved in 50 g of toluene, to which mixture are added 0.25 g of anhydrous copper(II)sulfate. The mixture is refluxed for 2 hours and the toluene then removed on a rotary evaporator. A yellow oil remains which after recrystallization from petrol ether yields 2.9 g of 3,5-dibromo-4-hydroxystyrene as white crystals, mp. 75° C.

What is claimed is:

1. A method for preparing 3-mono- and 3,5-dihalogenated 4-hydroxy and 4-acetoxystyrenes which comprises
   (a) halogenating a 4-hydroxyacetophenone with general formula

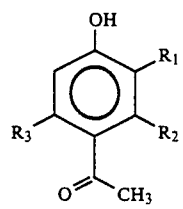

wherein
   $R_1$ is hydrogen or $C_1$ to $C_{10}$ alkyl; and
   $R_2$ and $R_3$ are independently hydrogen, alkyl, alkoxy, or halogen, wherein $R_1$ and $R_2$ may be combined to form a cycloaliphatic ring, consisting of 6 to 12 members,
   (b) esterification of the hydroxyl function to form a halogenated 4-acetoxyacetophenone derivative,
   (c) reduction of the ketone function to a hydroxyl function,
   (d) dehydration to form 3-mono or 3,5-dihalogenated 4-acetoxystyrene; with optional
   (e) hydrolysis to form the 3-mono or 3,5-dihalogenated 4-hydroxystyrene.

2. A method according to claim 1 wherein $R_1$ is hydrogen or ($C_1$-$C_3$) alkyl, and $R_2$ and $R_3$ are the same and are hydrogen, $C_1$-$C_3$ alkyl, $C_1$-$C_3$ alkoxy, or bromine.

3. A method according to claim 1 wherein step (b) is carried out with a halogen.

4. A method according to claim 1 wherein step (c), esterification, is carried out with acetyl chloride or acetic anhydride.

5. A method according to claim 1 wherein reduction is carried out either catalytically with hydrogen or with complex hydrides.

6. A method according to claim 1 wherein dehydration is carried out by heating under vacuum in the presence of a polymerization inhibitor and a dehydrating agent.

7. A method according to claim 1 wherein hydrolysis is carried out in an alkali or an acid.

* * * * *

UNITED STATES PATENT AND TRADEMARK OFFICE
CERTIFICATE OF CORRECTION

PATENT NO. : 4,933,495

DATED : 06-12-90

INVENTOR(S) : M. Aslam, et al.

It is certified that error appears in the above—identified patent and that said Letters Patent is hereby corrected as shown below:

Col. 2, Line 59, The compound "1-(3'-mono or 3',5'-disubstituted-4,-acetoxyphenyl)ethanol"
should read -- 1-(3'-mono or 3',5'-disubstituted-4'-acetoxyphenyl)ethanol --.

Col. 2, Line 66, Delete the "." after the word "process".

Col. 3, Line 12, The compound "3,5-disubstituted-4'-acetox-"
should read -- 3,5-disubstituted-4-acetox- --.

Col. 3, Line 14, The compound "1-(3,-mono or 3',5'-disubstituted-4'-acetoxyphenyl)ethanol"
should read -- 1-(3'-mono or 3',5'-disubstituted-4'-acetoxyphenyl)ethanol --.

Col. 3, Line 46, Compound description "4'acetoxyphenyl)ethanol"
should read -- 4'-acetoxyphenyl)ethanol --.

UNITED STATES PATENT AND TRADEMARK OFFICE
CERTIFICATE OF CORRECTION

PATENT NO. : 4,933,495

DATED : June 12, 1990

INVENTOR(S) : M. Aslam, et al

It is certified that error appears in the above-identified patent and that said Letters Patent is hereby corrected as shown below:

Col. 11, Line 58, The compound "1-(3',5'-dibromo-4,-hydroxyphenyl) ethanol"
should read -- 1-(3',5'-dibromo-4'-hydroxyphenyl) ethanol --.

Signed and Sealed this

Twenty-fifth Day of February, 1992

*Attest:*

HARRY F. MANBECK, JR.

*Attesting Officer*     *Commissioner of Patents and Trademarks*